United States Patent [19]
Schöneberg et al.

[11] Patent Number: 5,235,267
[45] Date of Patent: Aug. 10, 1993

[54] CIRCUIT AND A METHOD FOR MEASURING A QUANTITY INFLUENCING THE CAPACITANCE-VOLTAGE CHARACTERISTIC OF A CAPACITIVE ELEMENT

[75] Inventors: Uwe Schöneberg; Hosticka Bedrich, both of Duisburg, Fed. Rep. of Germany; Jordan Maclay, Maywood, Ill.; Günther Zimmer, Duisburg, Fed. Rep. of Germany

[73] Assignee: Fraunhofer-Gesellschaft zur Forderung der Angewandten Forschung E.V., Munich, Fed. Rep. of Germany

[21] Appl. No.: 768,440
[22] PCT Filed: Apr. 17, 1990
[86] PCT No.: PCT/EP90/00612
§ 371 Date: Sep. 25, 1991
§ 102(e) Date: Sep. 25, 1991
[87] PCT Pub. No.: WO90/13793
PCT Pub. Date: Nov. 15, 1990

[30] Foreign Application Priority Data
May 12, 1989 [DE] Fed. Rep. of Germany ....... 3915563

[51] Int. Cl.⁵ ............................................. G01N 27/00
[52] U.S. Cl. .................................. 324/71.5; 324/678; 422/82.02
[58] Field of Search .................. 324/71.1, 71.5, 663, 324/678; 422/82.02, 94; 436/151, 152

[56] References Cited
U.S. PATENT DOCUMENTS

| | | | |
|---|---|---|---|
| 4,112,356 | 9/1978 | Toy | 324/74.1 |
| 4,149,231 | 4/1979 | Bukosky et al. | 324/678 X |
| 4,166,974 | 9/1979 | Vermeers | 324/678 X |
| 4,636,714 | 1/1987 | Allen | 324/678 |
| 4,641,084 | 2/1987 | Komatsu | 324/71.5 |
| 4,831,325 | 5/1989 | Watson, Jr. | 324/678 |
| 5,103,183 | 4/1992 | Klein et al. | 324/663 |

FOREIGN PATENT DOCUMENTS 60-242354 4/1986 Japan.
2078970 1/1982 United Kingdom.

OTHER PUBLICATIONS

"Transition Metal-Gate MOS Gaseous Detectors", T. L. Poteat et al, IEEE Transactions on Electron Devices, vol. ED-29, No. 1, pp. 123–129, Jan. 1982.
"An Interface Circuit for Capacitive Sensors", T. Nagasawa et al, Transactions of the Institute of Electronics, vol. E70, No. 11, pp. 1049–1050, Nov. 1987.
"Sliding Capacitive Displacement Transducer", B. D. Bryner et al., NTIS Tech Notes, pp. 729–730, Aug. 1987.
Article entitled Hydrogen Sensitive MOS-Structures, Part 1, Principles and Applications by Ingemar Lundstrom, Sensors and Actuators, 1/ (1981) pp. 403–426.
MOS Hydrogen Sensors with Ultrathin Layers of Palladium, by G. Jordan Maclay, IEEE Transactions, vol. ED32, No. 7, Jul. 1985.

Primary Examiner—Kenneth A. Wieder
Assistant Examiner—Glenn Brown
Attorney, Agent, or Firm—Ralph H. Dougherty

[57] ABSTRACT

A circuit and a method for measuring a quantity influencing the capacitance-voltage characteristic of a capacitive element, the measuring accuracy and the signal-to-noise-ratio being improved by determining such quantity on the basis of the area under the curve of the capacitance-voltage characteristic.

18 Claims, 4 Drawing Sheets

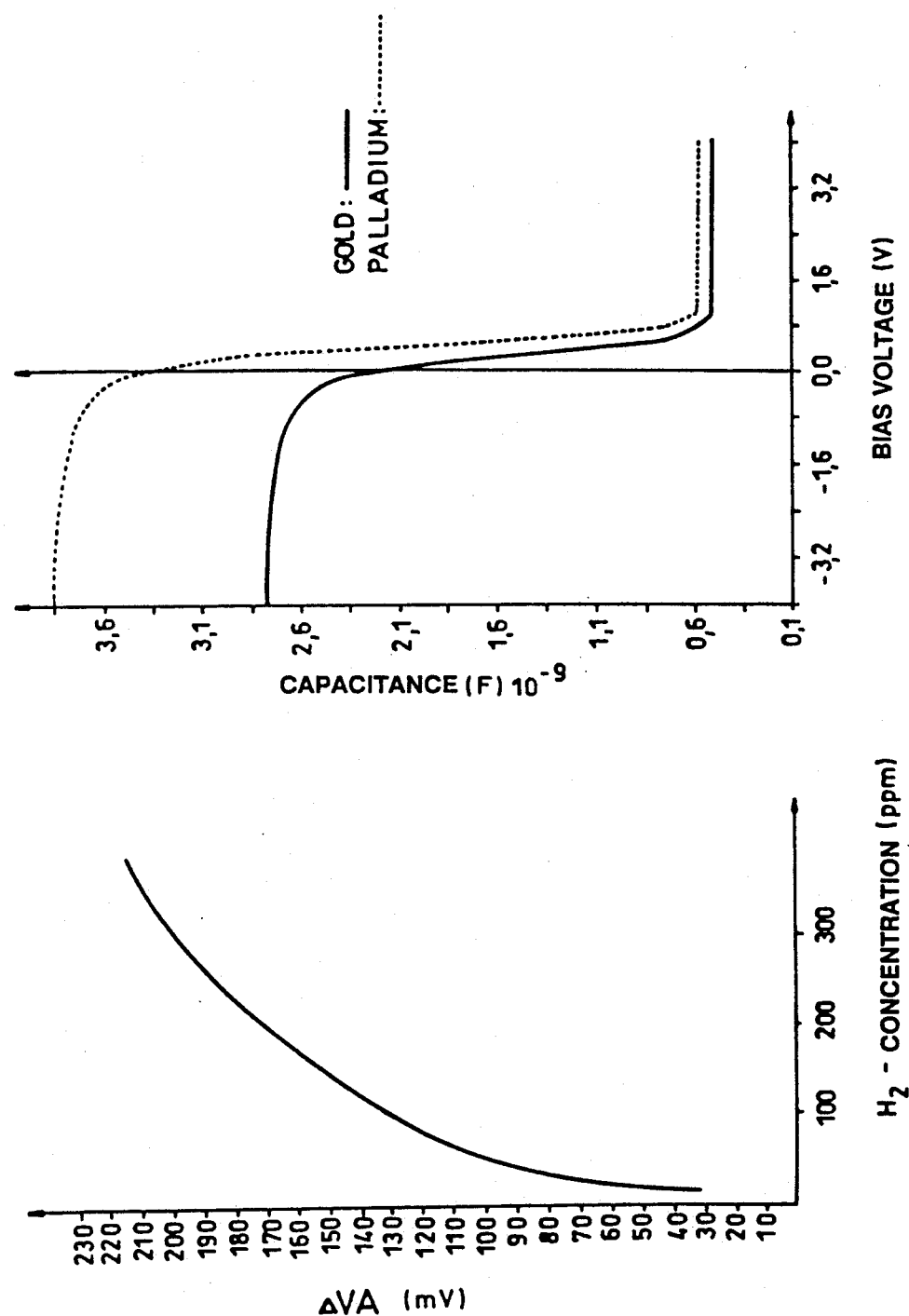

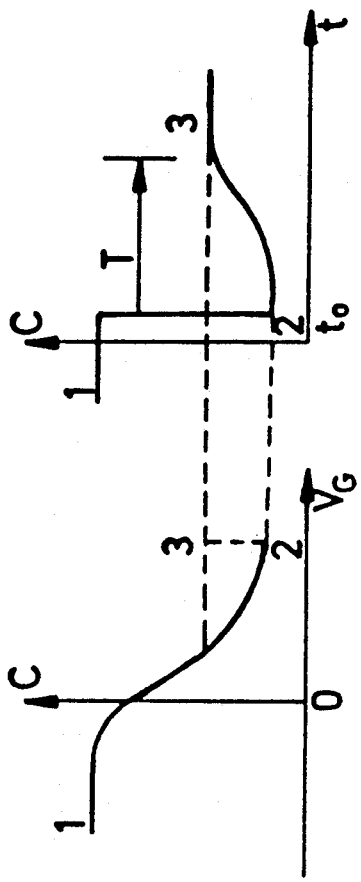
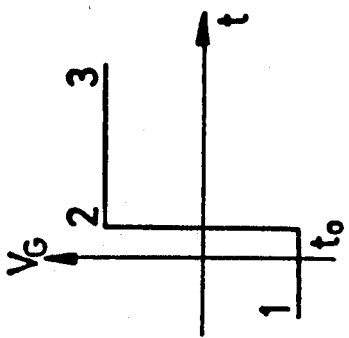
FIG. 6(a)  FIG. 6(b)  FIG. 6(c)

CIRCUIT AND A METHOD FOR MEASURING A QUANTITY INFLUENCING THE CAPACITANCE-VOLTAGE CHARACTERISTIC OF A CAPACITIVE ELEMENT

The present invention relates to a circuit for measuring a quantity influencing the capacitance-voltage characteristic of a capacitive element, as well as to a method of measuring a quantity influencing the capacitance-voltage characteristic of a capacitive element.

Capacitive MOS structures have a voltage-dependent capacitance value. The behavior of the capacitance-voltage curve is, e.g. in the case of capacitive MOS structures, influenced by additional quantities if the metallic layer consists of catalytic metals or contains at least a certain percentage of catalytic metals. This influence of specific quantities on the voltage-dependent capacitance behavior of such capacitive structures is utilized for constructing sensors adapted to be used for detecting the respective quantity which influences the voltage-dependent capacitance behavior.

Known fields of use of such capacitive elements are, for example, gas sensors responding to specific gases, e.g. hydrogen sensors. One embodiment of the last-mentioned hydrogen sensor whose voltage-dependent capacitance curve varies depending on the ambient humidity is disclosed in the scientific publication by G. J. Maclay, "MOS hydrogen sensors with ultrathin layers of palladium", IEEE Trans. Electron Devices, vol. ED-32, pages 1158 to 1164, 1985.

At present, two different techniques are used for detecting the change in the capacitance-voltage characteristic and, consequently, for determining the quantity influencing the capacitance-voltage characteristic:

In the first technique, which is known from "Sensors and Actuators, 1, 1981, pages 403 to 426", a constant bias voltage is applied to the capacitive MOS element, the constant bias voltage having superimposed on it a high-frequency voltage signal of predetermined amplitude. In the case of a displacement of the capacitance-voltage characteristic caused by the quantity to be measured, the capacitance will change at the working point determined by the bias voltage. This change in capacitance can be detected in a measuring bridge.

In the second technique, the capacitive MOS element in a feedback control circuit is subjected to a bias voltage of such nature that the capacitive MOS element has a constant capacitance value. The controlled bias voltage and/or the displacement of the voltage working point can be used for determining the quantity which influences the capacitance-voltage characteristic.

Both techniques described necessitate the use of a comparatively complicated circuit for detecting the quantity which influences the capacitance-voltage characteristic. In both techniques, migrations of ions can occur within the capacitive MOS structure in the interior of the structure and at the surface thereof, and this will impair the long-term stability as far as the detection of the quantity influencing the capacitance-voltage characteristic is concerned. Both techniques are based on the detection of a comparatively small signal variation in the working point. It follows that both techniques fail to have a sufficient signal-to-noise ratio with regard to the quantity determined, i.e. the humidity or the gas concentration.

Further distortions of the measuring results obtained using these known techniques come from the fact that the capacitance-voltage characteristic of the capacitive MOS element will normally not only depend on one quantity to be measured, but, to a certain extent, it will also be influenced by additional interference quantities.

In comparison with this prior art, the object of the present invention is further development of a circuit and a method of the type mentioned at the beginning, which are used for measuring a quantity influencing the capacitance-voltage characteristic of a capacitive element, in such a way that the accuracy in determining the influencing quantity can be improved still further.

In a circuit arrangement for measuring the concentration of a gas in a mixture of gases or the ion concentration in a liquid by means of a capacitive semiconductor element having a concentration-dependent capacitance-voltage characteristic, this object is achieved by a first voltage source ($V_s$) connected to one pole of the capacitive semiconductor element ($C_s$) for producing a first periodic voltage signal of predetermined amplitude, and an integrating circuit (OPV, $C_f$) connected to the other pole of the capacitive semiconductor element adapted to integrate the output current of the capacitive semiconductor element over part of the period of the first voltage signal, the concentration to be measured being determined by means of a relationship between the integrated value of the integrating circuit (OPV, $C_f$), and the concentration, such relationship being predetermined for the semiconductor element. In the case of a method for measuring the concentration of a gas in a mixture of gases or the ion concentration in a liquid by means of a capacitive semiconductor element having a concentration-dependent capacitance-voltage characteristic, this object is achieved by applying a periodic voltage signal of predetermined amplitude to the capacitive semiconductor element (Cs), detecting the area under the curve of the capacitance-voltage characteristic within a predetermined region by integration of the current of the capacitive semiconductor element over part of the period of the voltage signal, and determining the concentration to be measured on the basis of the detected area by means of a relationship between the concentration to be measured and the detected area, such relationship being predetermined for the semiconductor element.

The present invention is based on the finding that the lack of accuracy of the initially discussed methods of determining the quantity which influences the displacement of the capacitance-voltage characteristic of the capacitive element, and, especially, the insufficient signal-to-noise ratio in the case of a determination of said influencing quantity according to said known techniques will be avoided, provided that the area under the curve of the voltage-capacitance characteristic is used in a predetermined region as a basis for detecting said influencing quantity. Such a measurement can be implemented simply in circuitry by applying a periodic voltage signal of predetermined amplitude to the capacitive element, an integrating circuit integrating the output current of the capacitive element over a predetermined period of time. The resultant integrated value shows a predeterminable dependence on the influencing quantity so that it is, for example, possible to read out a table with said integrated value, the output value of said table being the influencing quantity. The resultant measuring circuit according to the present invention, which is used for carrying out said measuring method, consists essentially of a voltage source and of an integrating circuit with a capacitive element, which is adapted to be discharged via an electronic switch in the feedback branch, which gives the circuit a very simple structure. In the case of the influencing-quantity detection mode according to the present invention, the dynamic measurement is carried out with an A.C. component which moves around a working point. It is thus possible to suppress ion migrations within the capacitive element as well as on the surface thereof, whereby a long-term stability of the measuring result will be achieved. Deviating from the method described at the beginning, the influencing quantity is determined on the basis of the integral via the displaced capacitance-voltage curve, not simply on the basis of a detection of the change of the curve at a single voltage or capacitance point. In comparison with prior art, this will result in a substantially improved signal-to-noise ratio of the detected quantity causing the displacement of the capacitance-voltage characteristic.

Preferred further developments of the present invention are the subject matter of the subclaims.

The invention is better understood by referring to the drawings, which illustrate a preferred embodiment of the invented circuit, wherein:

FIG. 4 shows the dependence of the integration voltage on an influencing quantity in the case of the circuit according to FIG. 2.

FIG. 5 shows typical capacitance behaviors for capacitive MOS structures response to the bias voltage.

FIG. 6 (a through c) show voltage and capacitance behaviors.

Figure 1:
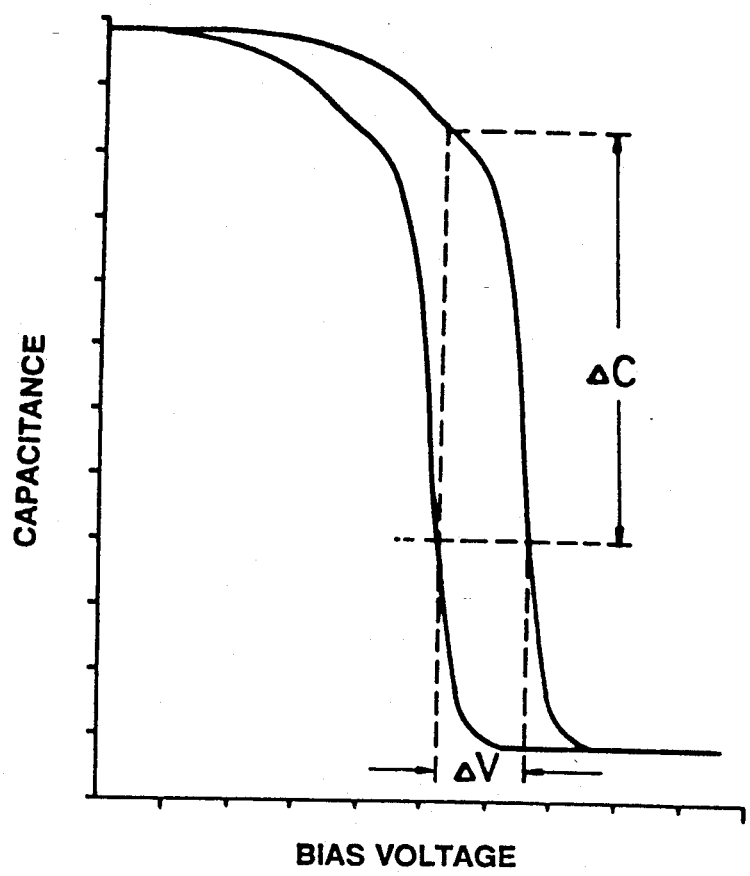
FIG. 1 shows a graphic representation of the capacitance-voltage characteristic of a capacitive element in the case of two different influencing quantities.

As can be seen in FIG. 1, the voltage-dependent capacitance behavior of a capacitive MOS structure, which has a catalytic metal on its metal layer, shifts in, response to an influencing quantity which can, for example, be the H$_2$-concentration or the concentration of a specific gas in the ambient atmosphere. As has been explained at the beginning, the prior art detected this displacement of the capacitance-voltage characteristic by measuring the change in capacitance $\Delta$ C in the case of a constant bias voltage or by measuring the change in the bias voltage $\Delta$ V while maintaining the capacitance value constant. In the case of the present invention, however, the influencing quantity is derived from the area under the voltage-capacitance curve within a predetermined region, as will be evident from the detailed explanation of the circuit and of the method following below.

Figure 2:
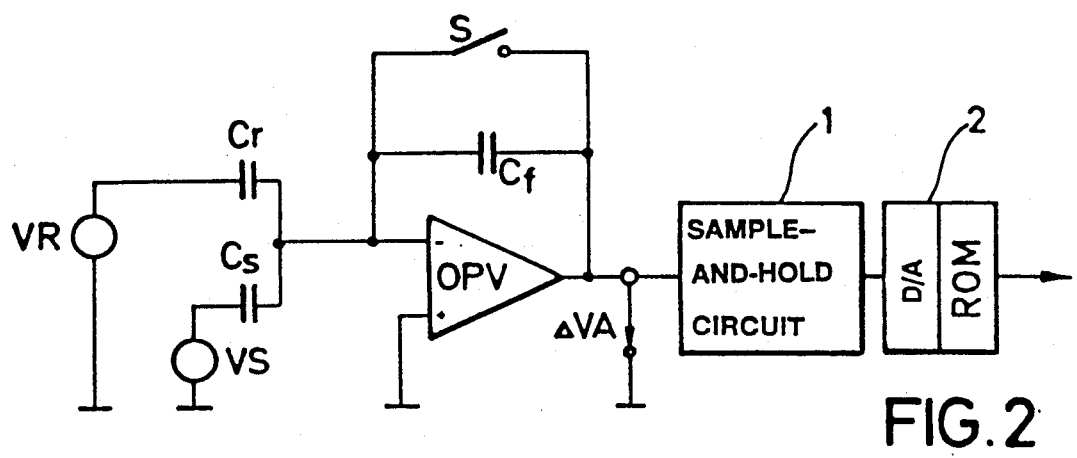
FIG. 2 shows a circuit diagram of the circuit according to the present invention used for measuring the quantity which influences the capacitance-voltage characteristic.

FIG. 2 shows a preferred embodiment of the circuit according to the present invention used for measuring a quantity influencing the capacitance-voltage characteristic of a capacitive element $C_s$, said quantity being, e.g., a ga concentration, which can be a hydrogen concentration, or an ion concentration in a liquid. The capacitive element $C_s$ in the case of said preferred embodiment is a capacitive MOS element whose metal layer consists of palladium, said element being also referred to as a MOS palladium gate sensor. The capacitive element $C_s$ is supplied with a square-wave voltage by a first voltage source VS, the amplitude of the square-wave voltage corresponding, in the case of a preferred embodiment, to $+/-$ b 1.5 V when the duty factor is 50 percent. The output side of the capacitive element $C_s$ is connected to the inverting input of an operational amplifier OPV. A second voltage source VR produces a second square-wave signal, which corresponds to the first square-wave, but is inverted relative thereto. This second square-wave voltage signal is applied to a reference capacitor $C_r$ whose output is also connected to the inverting input of the operational amplifier OPV. The capacitance of the reference capacitor $C_r$ is so selected that an offset voltage appearing at the output of the operational amplifier will be compensated when the capacitance-voltage characteristic of the capacitive element $C_s$ is not influenced by the quantity to be measured.

Figure 3:
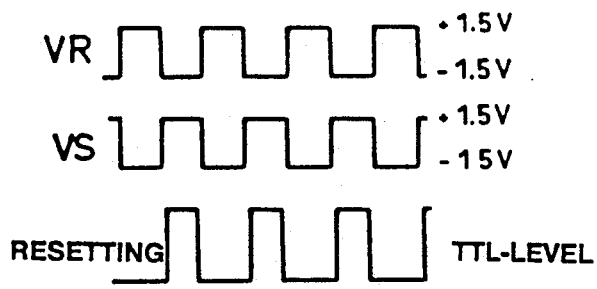
FIG. 3 shows signal curves of voltage signals of the type occurring in the circuit according to FIG. 2.

An integration capacitor $C_f$ is arranged in the feedback branch of the operational amplifier OPV, i.e. between its output and its inverting input, an electronic switch S being connected in parallel with said integration capacitor $C_f$. Said electronic switch S is operated in a specific, predetermined phase relationship to the phase of the first square-wave signal by means of a reset signal (cf. FIG. 3), whereby the integration will be finished and a voltage value at the output $\Delta$ VA will be reset. The output value of the operational amplifier OPV $\Delta$ VA prior to resetting will be transferred to a sample-and-hold circuit 1. This output value can concentration referred to in the example. Assignment of the Hz concentration to the output voltage $\Delta$ VA is appropriately made via a table, which can be implemented by a D/A converter and a ROM 2 storing the dependence of the quantities in question shown in FIG. 4. The curve shown in FIG. 4 is the result of a measurement with a palladium sensor whose catalytic metal layer is a palladium layer with a thickness of 21.1 nm (nanometer), which is arranged on a silicon dioxide layer with a thickness of 34 nm. A capacitive MOS structure with a gold gate with a thickness of 104.5 nm on a silicon dioxide insulating layer with a thickness of 34 nm was selected as a reference capacitor. The capacitance of the integration capacitor $C_f$ is 1 nF.

As has been stated above, the invented circuit detects the influencing quantity by means of integration of the capacitance-voltage curve of the capacitive element for the purpose of determining the area under the curve; this can be expressed by the following equation:

$$Q = \int C_s(U) \, dU \quad (1)$$

The current through the capacitive sensor element $C_s$ is given by:

$$i_s = dQ/dt = d/dt \int C_s(U) dU \quad (2)$$

Time integration at the feedback capacitor $C_f$ will result in the following output voltage:

$$VA = 1/C_f \int i_s \, dt = 1/C_f \int (C_s(U) - C_r) \, dU \quad (3)$$

The capacitance value $C_f$ must be so selected that the operational amplifier OPV will not be overdriven when the measured quantity has the maximum possible value.

FIG. 5 shows the two voltage-dependent capacitance curves of the reference element C, and of the sensor element $C_s$. As can be seen in FIG. 5, the non-optimum adaptation of the two curves will result in an offset voltage of approximately 2 V. This offset voltage was taken into consideration with regard to the curve according to FIG. 4.

When looking at the circuit according to FIG. 2, it will become evident that the invented method, which is used for measuring the quantity influencing the capacitance-voltage characteristic, permits a compensation of interference quantities influencing both the actual sensor element or capacitive element $C_s$ as well as the reference capacitor C, with regard to their respective capacitance-voltage characteristic. If, for example, the capacitive (sensor) element $C_s$ depends with regard to its capacitance-voltage characteristic on a quantity A as well as on an interference quantity B, it will be possible to compensate this undesirable sensitivity to said interference quantity B when the reference capacitor is a capacitive MOS element, which is only sensitive to said interference quantity B. Complete compensation with regard to said interference quantity B will be possible through suitable dimensioning of the two capacitive elements. Using a plurality of reference elements, it will be possible to compensate a corresponding number of undesirable cross sensitivities.

The frequency of the square-wave signals is preferably within the kHz range. Hence, the cycle of the square-wave voltage signals will be longer than the minority carrier reaction time so that an equilibrium state of the minority carrier accumulation will occur, while the cycle of the square-wave voltage signals is shorter than the minority carrier generation recombination time so that the MOS structure will not get into the equilibrium inversion region. This will result in an amplification of the signal, since the voltage-dependent capacity curve runs downward into the region of deep charge carrier depletion.

When setting the cycle, it is necessary to tkae into account the behavior of the MOS capacitor in the region of deep charge carrier depletion. After the application of a step voltage, the MOS capacitor only remains in the region of deep charge carrier depletion for a specific time T, and then it changes to the HF inversion curve.

$$T = 2\tau N_B / n_i.$$

wherein $\tau$ is the minority carrier lifetime, $N_B$ the doping and $n_i$ the intrinsic concentration for the MOS capacitor in question.

The clock rate can either be selected so high that a movement occurring in the direction towards the HF inversion curve and influencing the accuracy will not yet take place, or it can be selected so that the HF inversion curve is certain to be reached. For the sake of clarity, reference is made to FIG. 6 in which:

(a) shows the time-dependent gate voltage at the MOS capacitor, (b) shows the voltage-dependent capacitance of said MOS capacitor at the times 1, 2, 3 according to FIG. 6(a), and (c) shows the time-dependent capacitance behavior.

Preferably, the period of duration of the voltage signal is longer than the minority carrier reaction time in the capacitance semiconductor element so that an equilibrium state of the minority carrier accumulation will occur, and shorter than the minority carrier recombination time.

In the embodiment described, a capacititive MOS structure provided with a palladium gate is used as a humidity sensor. However, the invented method can also be used for gas sensors having an MOS structure for evaluating the gas concentration as well as for measuring other quantities which influence the capacitance-voltage characteristic of a capacitive element.

We claim:

1. A method for measuring the concentration of a gas in a mixture of gases by means of a capacitive semiconductor element having a capacitance-voltage characteristic depending on the gas concentration, comprising the steps of:

applying to the capacitive semiconductor element ($C_s$) a periodic voltage signal of predetermined amplitude, detecting the area under the curve of the capacitance-voltage characteristic by integration of the current of the capacitive semiconductor element over part of the period of the voltage signal, and determining the gas concentration to be measured on the basis of the detected area by means of a relationship between the gas concentration to be measured and said area, said relationship being determined in advance for the semiconductor element ($C_s$).

2. A method according to claim 1 wherein the area in detected by integration of the output current of the capacitive semiconductor element ($C_s$) over part of the period of the voltage signal.

3. A method according to claim 1 wherein the period duration of the voltage signal is longer than the minority carrier reaction time in the capacitive semiconductor element ($C_s$) so that an equilibrium state of the minority carrier accumulation will occur, and shorter than the minority carrier recombination time.

4. A method for measuring the ion concentration in a liquid by means of a capacitive semiconductor element having a capacitance-voltage characteristic depending on the ion concentration, comprising the steps of:

applying to the capacitive semiconductor element ($C_s$) a periodic voltage signal of predetermined amplitude, detecting the area under the curve of the capacitance-voltage characteristic by integration of the current of the capacitive semiconductor element over part of the period of the voltage signal, and determining the ion concentration to be measured on the basis of the detected area by means of a relationship between the ion concentration to be measured and said area, said relationship being determined in advance for the semiconductor element ($C_s$).

5. A method according to claim 4 wherein the area is detected by integration of the output current of the capacitive semiconductor element ($C_s$) over part of the period of the voltage signal.

6. A method according to claim 4 wherein the period duration of the voltage signal is longer than the minority carrier reaction time in the capacitive semiconductor element ($C_s$) so that an equilibrium state of the minority carrier accumulation will occur, and shorter than the minority carrier recombination time.

7. A circuit arrangement for measuring the concentration of a gas in a mixture of gases by means of a capacitive semiconductor element having a capacitance-voltage characteristic depending on the gas concentration, comprising:

a first voltage source ($V_s$) connected to one pole of the capacitive semiconductor element ($C_s$) and used for producing a first periodic voltage signal of predetermined amplitude, and an integrating circuit (OPV, $C_f$), which is connected to the other pole of the capacitive semiconductor element ($C_s$) and which integrates the output current of said capacitive semiconductor element ($C_s$) over part of the period of said first voltage signal, the gas concentration to be measured being determined by means of a relationship between the integrated value of the integrating circuit (OPV, $C_f$) and said gas concentration, said relationship being determined in advance for the semiconductor element ($C_s$).

8. A circuit arrangement according to claim 7 wherein the capacitive semiconductor element ($C_s$) is a MOS structure whose metal layer consists of a catalytic metal or contains at least a certain percentage of said catalytic metal.

9. A circuit arrangement according to claim 7 wherein the capacitive semiconductor element ($C_s$) is a capacitive MOS gas sensor.

10. A circuit arrangement according to claim 7 wherein the capacitive semiconductor element ($C_s$) is a capacitive MOS humidity sensor.

11. A circuit arrangement according to claim 7 wherein the capacitive semiconductor element ($C_s$) is a capacitive MOS sensor for measuring ion concentrations in liquids.

12. A circuit arrangement according to claim 7 wherein the first voltage source ($V_s$) produces a periodic square-wave signal.

13. A circuit arrangement according to claim 7 wherein the integrating circuit (OPV, $C_f$) comprises an operational amplifier (OPV), a parallel connection consisting of an integration capacitor ($C_f$) and of an electronic switch (S) being disposed in the feedback branch of said operational amplifier (OPV), the electronic switch (S) is controlled in a fixed phase relationship to the phase of the periodic signal by the first voltage source ($V_s$) and a terminal of the capacitive semiconductor element ($C_s$) is connected to an input of the operational amplifier (OPV).

14. A circuit arrangement according to claim 7 further comprising a second voltage source (VR) for producing a second voltage signal which is inverted relative to said first voltage signal and a reference capacitor ($C_r$) whose capacitance is chosen such that an offset voltage at the output of the integrating circuit (OPV, $C_f$) is compensated when the capacitance-voltage characteristic of the capacitive semiconductor element ($C_s$) is uninfluenced by the gas concentration to be measured, said reference capacitor ($C_r$) being connected to the second voltage source (VR) on the one hand and to the integrating circuit (OPV, $C_f$) on the other.

15. A circuit arrangement according to claim 7 further comprising a capacitive reference element ($C_r$) whose capacitance voltage characteristic is influenced by an interference quantity to essentially the same extent as that of the capacitive element ($C_s$), the capacitance-voltage characteristic of said capacitive reference element ($C_r$) depending, however, not on the gas concentration to be measured, and a second voltage source (VR), which is used for producing a second voltage signal inverted relative to said first voltage signal and which is connected to a terminal of the reference element ($C_r$) whose other terminal is connected to the integrating circuit (OPV, $C_f$).

16. A circuit arrangement for measuring the ion concentration in a liquid by means of a capacitive semiconductor element having a capacitance-voltage characteristic depending on the ion concentration, comprising:

a first voltage source ($V_s$) connected to one pole of the capacitive semiconductor element ($C_s$) and used for producing a first periodic voltage signal of predetermined amplitude, and an integrating circuit (OPV, $C_f$), which is connected to the other pole of the capacitive semiconductor element ($C_s$) and which integrates the output current of said capacitive semiconductor element ($C_s$) over part of the period of said first voltage signal, the ion concentration to be measured being determined by means of a relationship between the integrated value of the integrating circuit (OPV, $C_f$) and said ion concentration, said relationship being determined in advance for the semiconductor element ($C_s$).

17. A circuit arrangement according to claim 16 further comprising a second voltage source (VR) for producing a second voltage signal which is inverted relative to said first voltage signal and a reference capacitor ($C_r$) whose capacitance is chosen such that an offset voltage at the output of the integrating circuit (OPV, $C_f$) is compensated when the capacitance-voltage characteristic of thee capacitive semiconductor element ($C_s$) is uninfluenced by the ion concentration to be measured, said reference capacitor ($C_r$) being connected to the second voltage source (VR) on the one hand and to the integrating circuit (OPV, $C_f$) on the other.

18. A circuit arrangement according to claim 16 further comprising a capacitive reference element ($C_r$) whose capacitance-voltage characteristic is influenced by an interference quantity to essentially the same extent as that of the capacitive element ($C_s$), the capacitance-voltage characteristic of said capacitive reference element ($C_r$) depending, however, not on the gas concentration to be measured, and a second voltage source (VR), which is used for producing a second voltage signal inverted relative to said first voltage signal and which is connected to a terminal of the reference element ($C_r$) whose other terminal is connected to the integrating circuit (OPV, $C_f$).

* * * * *